(12) United States Patent
Archer et al.

(10) Patent No.: US 7,914,587 B2
(45) Date of Patent: Mar. 29, 2011

(54) WRIST DEVICE FOR USE WITH A PROSTHETIC LIMB

(75) Inventors: Shawn L. Archer, Salt Lake City, UT (US); Arthur D. Dyck, Draper, UT (US); Reed H. Grant, Salt Lake City, UT (US); Edwin K. Iversen, Holladay, UT (US); Joseph A. Jacobs, Salt Lake City, UT (US); Steven R. Kunz, Salt Lake City, UT (US); James R. Linder, West Jordan, UT (US); Harold H. Sears, Salt Lake City, UT (US)

(73) Assignee: Motion Control, Salt Lake City, UT (US)

( * ) Notice: Subject to any disclaimer, the term of this patent is extended or adjusted under 35 U.S.C. 154(b) by 1148 days.

(21) Appl. No.: 11/567,155

(22) Filed: Dec. 5, 2006

(65) Prior Publication Data
US 2007/0173955 A1 Jul. 26, 2007

Related U.S. Application Data

(63) Continuation-in-part of application No. 10/618,525, filed on Jul. 11, 2003, now Pat. No. 7,144,430.

(60) Provisional application No. 60/395,718, filed on Jul. 12, 2002.

(51) Int. Cl.
*A61F 2/68* (2006.01)
*A61F 2/58* (2006.01)

(52) U.S. Cl. ............................................. 623/62; 623/61

(58) Field of Classification Search ............... 623/61–62
See application file for complete search history.

(56) References Cited

U.S. PATENT DOCUMENTS

| 2,812,961 A | | 11/1957 | Brown et al. | |
|---|---|---|---|---|
| 5,447,403 A | * | 9/1995 | Engler, Jr. | 414/4 |
| 5,728,175 A | * | 3/1998 | Rincoe | 623/49 |

* cited by examiner

*Primary Examiner* — David Isabella
*Assistant Examiner* — Jacqueline Woznicki
(74) *Attorney, Agent, or Firm* — Thorpe North & Western LLP (57) ABSTRACT

A multi-axis wrist device is provided for use with a prosthetic limb. The wrist device includes a base plate that is configured for attachment to a prosthetic limb. A cross piece, having first and second axes, can be coupled to the base plate. A prosthetic attachment can be coupled to the cross piece. The cross piece can enable a user to simultaneously flex the prosthetic attachment in two different axes. A first and second torsional spring can be coupled to the first and second axes, respectively, to enable the prosthetic attachment to be biased toward a center point.

15 Claims, 8 Drawing Sheets

WRIST DEVICE FOR USE WITH A PROSTHETIC LIMB

CROSS-REFERENCE TO RELATED APPLICATIONS AND CLAIM OF PRIORITY

This is a continuation-in-part of U.S. patent application Ser. No. 10/618,525 filed on Jul. 11, 2003 (U.S. Pat. No. 7,144,430) which claims priority to U.S. Provisional application No. 60/395,718 filed on Jul. 12, 2002.

FIELD OF THE INVENTION

The present invention relates generally to wrist devices for use with prosthetic limbs.

BACKGROUND OF THE INVENTION

There are thousands of individuals with absences of arms or hands in the United States alone and thousands of new amputees each year. Many of these amputees are fitted with electrically powered hand and arm prostheses. The utility of an electric hand prosthesis is greatly enhanced by the ability to rotate and flex the hand prosthesis. Once an object is grasped with a prosthetic hand, the object can be oriented for a desired task if the prosthesis can rotate and flex. A below the elbow amputee usually has four degrees of freedom available, which are humeral flexion/extension, abduction/adduction, rotation and elbow flexion. To orient an object into an arbitrary orientation, two or more degrees of freedom are essential. Also, simple tasks like holding a fork or a tray of food in the needed orientation are difficult to do without wrist flexion/extension.

Wrist rotation and wrist flexion allow the amputee to better orient grasped objects. Wrist rotation alone is not enough to provide this flexibility that most prosthesis users desire. However, currently available wrist flexion devices are heavy, long, and are not easily locked in position. Currently available wrist rotators and flexion devices can add several inches of length and several ounces of weight, making the prosthesis awkward and cumbersome. Some known rotators can add about 2.5 inches and 3.5 ounces to the weight of the prosthesis. Adding a wrist flexion device that is currently commercially available can add another 1 or 2 inches and 2 or 3 ounces. This means an addition of approximately 4 inches and 6 ounces to get both rotation and flexion. Four inches in the wrist area is too long for most amputees to use with ease, especially amputees who have retained most of their forearm. For this reason, few amputees utilize two or three degree-of-freedom wrists. This generally limits the usefulness of the prosthesis.

SUMMARY OF THE INVENTION

A multi-axis wrist device is provided for use with a prosthetic limb. The wrist device includes a base plate that is configured for attachment to a prosthetic limb. A cross piece, having first and second axes, can be coupled to the base plate. A prosthetic attachment can be coupled to the cross piece. The cross piece can enable a user to simultaneously flex the prosthetic attachment in two different axes. A first and second torsional spring can be coupled to the first and second axes, respectively, to enable the prosthetic attachment to be biased toward a center point.

DETAILED DESCRIPTION

Reference will now be made to the exemplary embodiments illustrated in the drawings, and specific language will be used herein to describe the same. It will nevertheless be understood that no limitation of the scope of the invention is thereby intended. Alterations and further modifications of the inventive features illustrated herein, and additional applications of the principles of the inventions as illustrated herein, which would occur to one skilled in the relevant art and having possession of this disclosure, are to be considered within the scope of the invention.

The present invention provides a wrist device for use with a prosthetic limb. The wrist device of the present invention can provide many advantages for amputees because the wrist device is lightweight and compact relative to the wrist devices presently available. For example, the wrist device includes a semi-cylindrical rotator that allows the wrist to exhibit compliance in flexion and extension directions while adding relatively little length and weight to the device. The utility of the wrist device is further increased by a sliding lock mechanism that does not add a significant amount of weight or length to the device. An amputee can lock the wrist device in a desired position with the sliding lock mechanism, which helps the amputee in using a mechanical hand to grasp objects.

Figure 1:
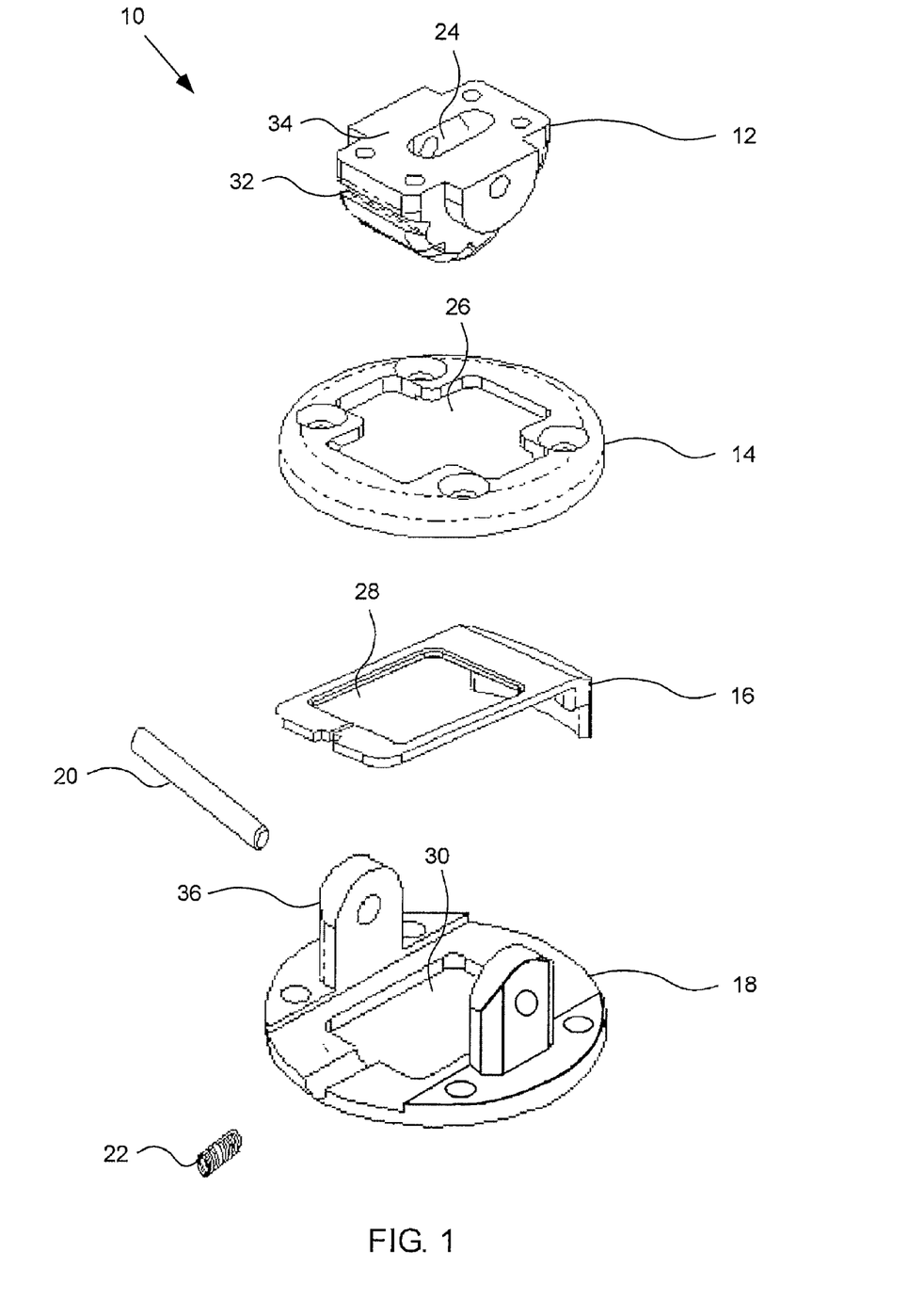
FIG. 1 is a perspective view of a wrist device in accordance with an embodiment of the present invention.

As shown in FIG. 1, the wrist device 10 includes a base plate 18 with an opening 30. The base plate is configured to be connected to a prosthetic limb, such as a prosthetic arm. A semi-cylindrical rotator 12 gives the wrist the ability to rotate in a flexion or extension direction. A top portion 34 of the semi-cylindrical rotator is configured for connection to a prosthetic hand. The cylindrical portion of the rotator has a plurality of slots 32 that are configured to receive a sliding lock plate 16. The sliding lock plate is slidably engaged with the base plate in order to lock into the slots of the semi-cylindrical rotator. The sliding lock plate also includes an opening 28. In one embodiment of the invention, the sliding lock plate is coupled to the base plate so that the sliding lock plate's opening is aligned with the base plate's opening in a manner that allows the semi-cylindrical rotator to at least partially pass through the base plate and the sliding lock plate. The opening in the base plate can be in a central portion of the base plate, and the opening in the sliding lock plate can be in a central portion of the sliding lock plate, according to one embodiment of the invention.

The relatively short height of the present invention can be achieved in part by utilizing a sliding lock plate that is thin relative to the locking pins or clamping balls that have been used in the past. Although the sliding lock plate is relatively thin, the sliding lock plate is still strong enough to be used effectively and safely in the wrist device. The strength of the locking device is maximized by minimizing the gap between the semi-cylindrical rotator and the base plate. Furthermore, the portion of the sliding lock plate that comes in contact with the semi-cylindrical rotator can be made to extend the full width of the wrist, which provides additional locking strength.

In one embodiment of the invention, a cover plate 14 with an opening 26 is coupled to the base plate 18 over the sliding lock plate 16 in a manner that limits movement of the sliding lock plate to sliding between the base plate and cover plate. In another embodiment, the base plate is configured to limit movement of the sliding lock plate so that the sliding lock plate always remains flush against the base plate.

The semi-cylindrical rotator is coupled to the base plate in a manner that allows the rotator to rotate around an axis. This can be accomplished by configuring the base plate to include two supporting arms 36 with holes that can receive a pivot pin 20. The pivot pin is coupled to these supporting arms and passes through a hole in the semi-cylindrical rotator 12. In a different embodiment, instead of having supporting arms, the base plate can be configured to directly receive the pivot pin. When the invention includes a cover plate 14, the cover plate can also be configured to receive the pivot pin in a manner that would allow the semi-cylindrical rotator to turn. Alternatively, the cover plate and the base plate can be configured to allow the pivot pin to sit between them.

A primary latch return spring 22 can be connected to the base plate 18 and to the sliding lock plate 16. The spring presses against the sliding lock plate and biases the sliding lock plate in a locked position. In the locked position, the sliding lock plate is engaged with the semi-cylindrical rotator 12 to prevent the semi-cylindrical rotator from rotating. When an amputee presses on the sliding lock plate, the plate can disengage from the slots 32 in the semi-cylindrical rotator and allow the semi-cylindrical rotator the freedom to rotate.

The opening in the base plate and the opening in the sliding lock plate allow for a minimization of the height of the device. The semi-cylindrical rotator can pass at least partially through the opening in the base plate and the opening in the sliding lock plate. This allows the height of the wrist device to be minimized because the rotator's full height is not added to the height of the device. When the wrist device uses a cover plate, the semi-cylindrical rotator can be coupled to the base plate so that the semi-cylindrical rotator passes through the opening in the cover plate. When configured in this manner, the height of the wrist device is small enough to make the wrist device useful for practically any amputees desiring to use a mechanical hand.

Figure 2:
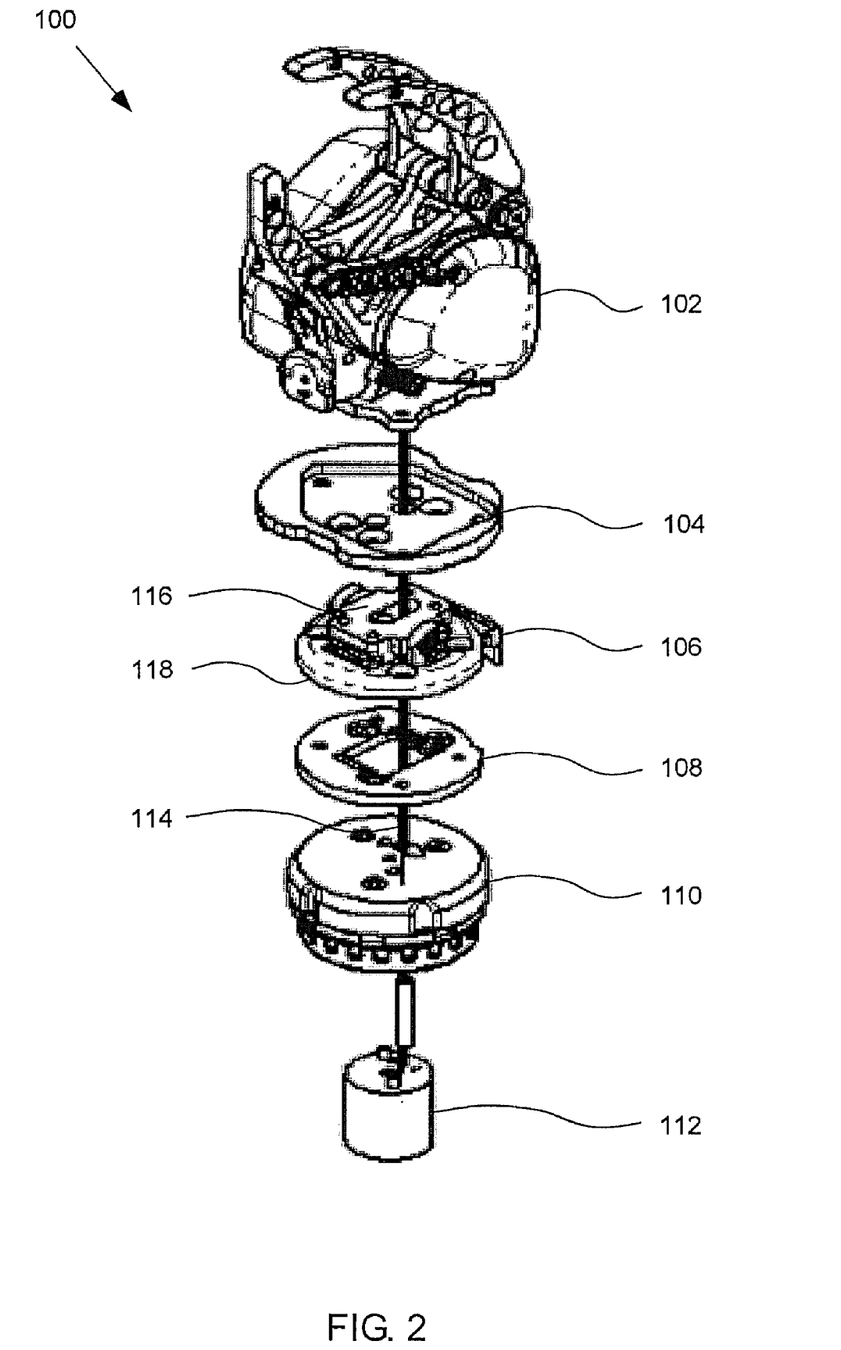
FIG. 2 is a perspective view of a prosthetic hand device according to an embodiment of the present invention.

The prosthetic wrist device can be included as part of a prosthetic arm device 100, as shown in FIG. 2. The prosthetic wrist includes a base plate 118 and a sliding lock plate 106 coupled to the base plate. As previously mentioned, a semi-cylindrical rotator 116 with slots is coupled to the base plate so that the sliding lock plate will lock into the slots of the semi-cylindrical rotator. A lower mounting plate 108 is coupled to the base plate. A wrist quick disconnect unit 110 is coupled to the lower mounting plate, and an upper mounting plate 104 is coupled to the semi-cylindrical rotator. The prosthetic wrist device also includes a prosthetic hand 102 that is coupled to the upper mounting plate. Additionally, a coax connector 112 can be coupled to the wrist quick disconnect unit.

A bundle of wires 114 is coupled to the coax connector and routed through the wrist disconnect unit, the lower mounting plate, the base plate, the sliding lock mechanism, the semi-cylindrical rotator, and the upper mounting plate. The bundle of wires is then coupled to the prosthetic hand so that it can carry control signals to the hand.

Figure 3:
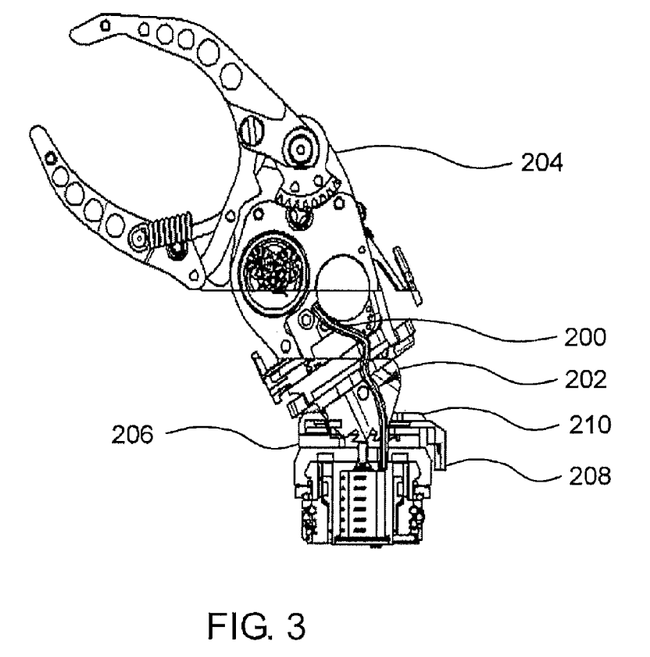
FIG. 3 is a cross sectional view of an embodiment of the invention for a prosthetic device with flexion and extension movement.

FIG. 3 shows a cross sectional view of wires routed through the wrist device. The prosthetic hand 204 attached to the semi-cylindrical rotator 202 can be a mechanical hand that receives electrical control signals. The wires 200 can be routed through the opening in the base plate 206, the opening in the sliding lock plate 208, the opening in the cover plate 210, and the opening in the central portion of the semi-cylindrical rotator. The wires can be routed through the rotator in such a way as to allow the wires to travel close to the neutral axis. This ensures that the wires are minimally stressed and at the same time protected from being snagged or crushed by contact with the environment. This may include wrapping the wires around the neutral axis to reduce the effect of repetitive flexing on the wires. Multi-strand wires can also be used because they tolerate repetitive flexing better than single strand wires.

Figure 4:
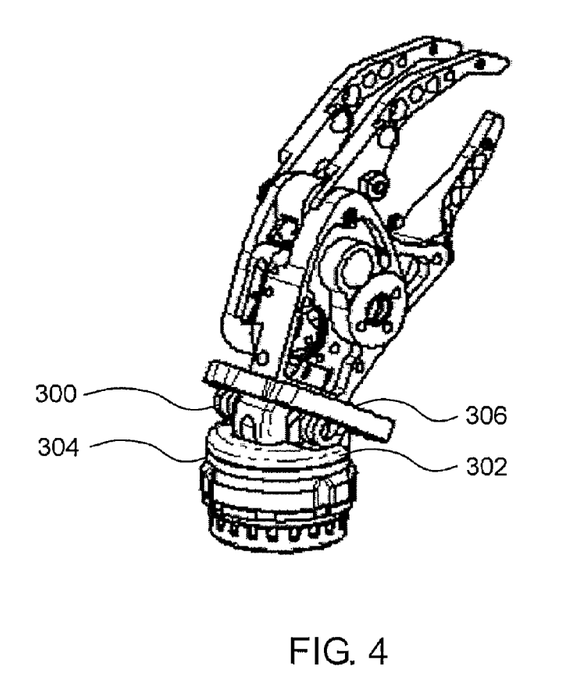
FIG. 4 is a perspective view of an embodiment of the present invention for a prosthetic device with flexion and extension movement.
Figure 5:
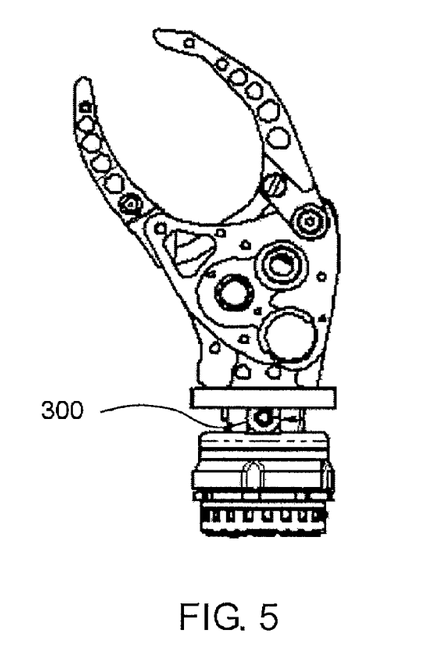
FIG. 5 is a side view of an embodiment of the invention for a prosthetic device with flexion and extension.
Figure 6:
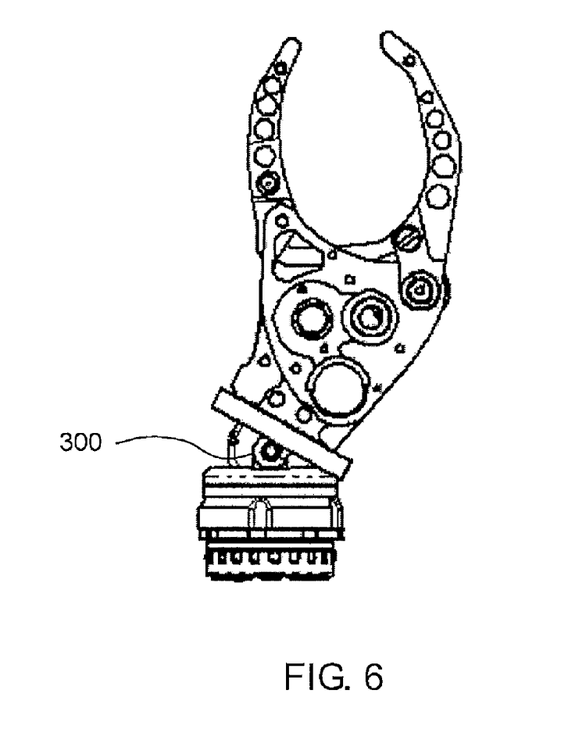
FIG. 6 is a side view of an embodiment of the invention for a prosthetic device with flexion and extension.
Figure 7:
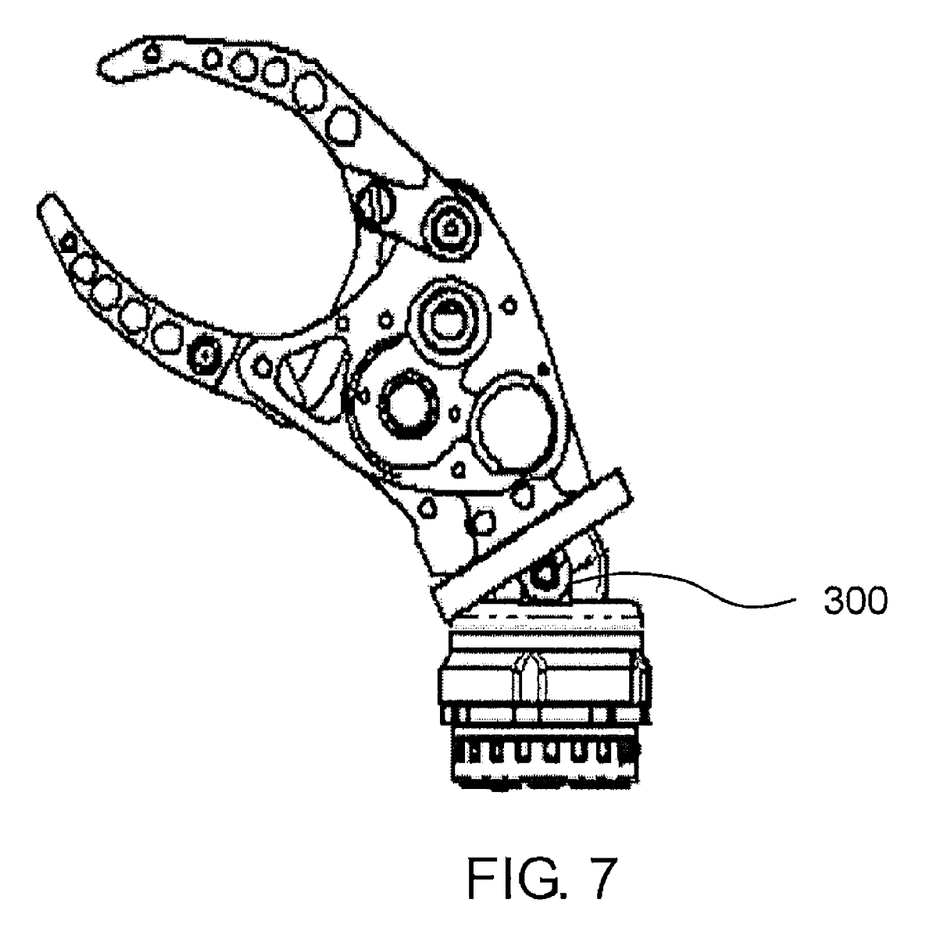
FIG. 7 is a side view of an embodiment of the invention for a prosthetic device with flexion and extension.

FIG. 4, FIG. 5, FIG. 6, and FIG. 7 show an embodiment of the present invention that includes a torsional spring 300 and a locking rotator structure with a sliding lock mechanism and a semi-cylindrical rotator with locking slots. One end of the torsional spring can be coupled to either the base plate 304 or the cover plate 302, and the other end is attached to the upper mounting plate 306. The torsional spring can be configured to allow a locking wrist rotator structure to exhibit compliance in an extension or flexion direction, and then return the wrist device to an upright position. FIG. 4 shows a torsional spring 300 in the present invention in a perspective view. FIG. 5 shows the wrist device held in an upright position, FIG. 6 shows the wrist device rotated in an extension direction, and FIG. 7 shows the wrist device rotated in a flexion direction.

The prosthetic device can also include a secondary latch that holds the sliding lock plate in an unlocked position and allows free compliant flexion and extension movement of the prosthetic limb. The secondary latch can be a ring configured to slide over the sliding lock mechanism, according to one embodiment of the present invention. This secondary latch allows a prosthesis user to grasp objects without loosening their grip when the wrist rotates. For example, the prosthesis user can close a door by grasping the door knob securely with a prosthetic hand, and even while the door swings closed the compliant wrist is passively flexed to allow the grasp to remain secure. The wrist device of the present invention provides a lightweight prosthetic joint that can exhibit compliance in the flexion and extension directions, but the device does not make a prosthetic arm too long to be useful to an amputee.

In another embodiment, the wrist device can be configured to enable an additional degree of freedom. In addition to the wrist flexion/extension and rotation axes, an abduction/adduction axis can be added to allow the wrist to rotate as well as exhibit compliance in three dimensions, allowing more natural movement of the wrist.

Figure 8:
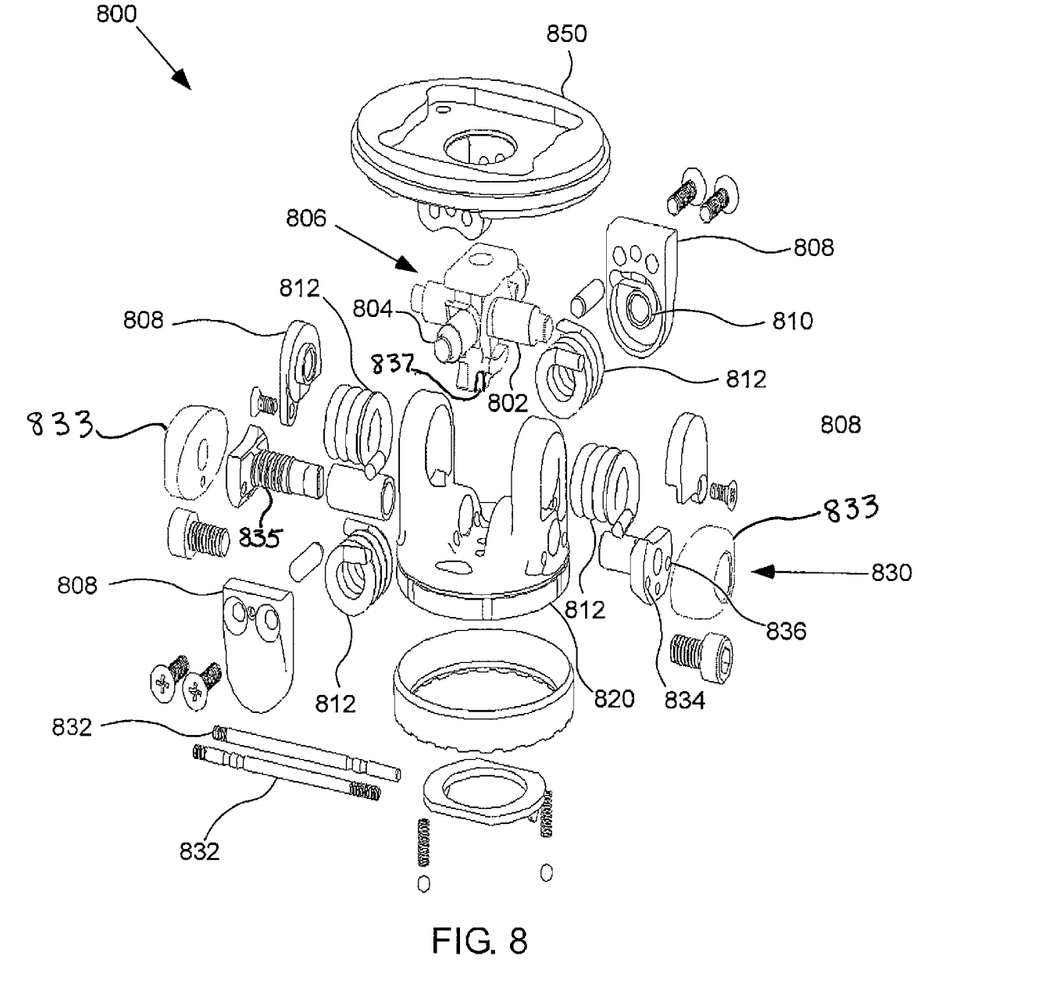
FIG. 8 is a perspective view of a multi-flex wrist device in accordance with an embodiment of the present invention.

A multi-flex wrist 800 is a prosthetic device which allows the wearer to flex their prosthetic hand or terminal device in two different axes at the same time. In one embodiment, as shown in FIG. 8, the pivot for the wrist includes a first axis 802 and a second axis 804 crossing at a point and forming a plus (+) shaped structure referred to as a cross piece 806 that incorporates both axes. In one embodiment, the cross piece can function similar to a universal joint to enable the wrist to pivot in each direction. Alternatively, two separate axes that are not inter-connected can be used. Each side of the multi-flex wrist can be attached to one of the axes by a clevis 808 and bushing 810 at each end of the axis which allows rotation about that axis. Between the clevis and the center of the cross piece a spring 812 attaches and allows flexion in both directions of the particular axis so that the spring normally centers the axis at a neutral point. In one embodiment, the spring can be a torsional spring, though other spring configurations are possible. The neutral point can be a centered location that enables a prosthetic attachment to the multi-flex wrist to be substantially parallel with a user's forearm. The torsion springs surround the axes of the cross piece and engage with the center of the cross in the center and the clevis piece on the outside.

The cross piece 806 may also include a locking mechanism 830 that allows one axis to be locked in one or more positions. Alternatively, there may be two locking mechanisms to allow locking of both axes. The locking mechanism can include at least one spring loaded lock pin 832. The spring loaded lock pin enables the locking mechanism to be activated or de-activated without having the wrist properly aligned to lock or unlock. The lock mechanism can be guided and aligned by two pins 832 attached between the lock and unlock buttons 833. For example, in the embodiment shown in FIG. 8, the pins can be inserted into a first location 834 and a second location 836. These two pins have the further function of holding the lock pin biased in one direction or the other by spring loaded detents in the pins.

The locking mechanism 830 can be activated or deactivated by a user. When the wrist is then moved such that the lock pin 832 becomes aligned with a corresponding locking slot 837, then the spring loaded lock pin 835 can be engaged or removed from the locking slot. This makes it easier to lock or unlock as the wrist does not have to be exactly aligned in order for the pin to engage. The spring loaded lock mechanism also provides the feature where unlocking the wrist doesn't have to happen immediately upon actuating the lock pin. The lock pin will be disengaged from its slot only when the load on the pin is removed and the pin allowed to be pulled free with the spring. If this were not the case, a large force would be necessary to unlock the wrist if the hand were supporting a heavy load. That is both a safety and a convenience feature.

The multi-flex wrist is also configured to enable a user to change the springs 812 when desired. Each spring can be changed one at a time and the mechanism will stay together sufficiently to allow the change.

Wires 200 from the prosthetic hand, as shown in FIG. 3 can be routed through the opening in the base plate 820, as shown in FIG. 8. The wires can be routed through the opening in such a way as to allow the wires to travel close to the neutral axis. This ensures that the wires are minimally stressed and at the same time protected from being snagged or crushed by contact with the environment. This may include wrapping the wires around the neutral axis to reduce the effect of repetitive flexing on the wires. Multi-strand wires can also be used because they tolerate repetitive flexing better than single strand wires.

Figure 9:
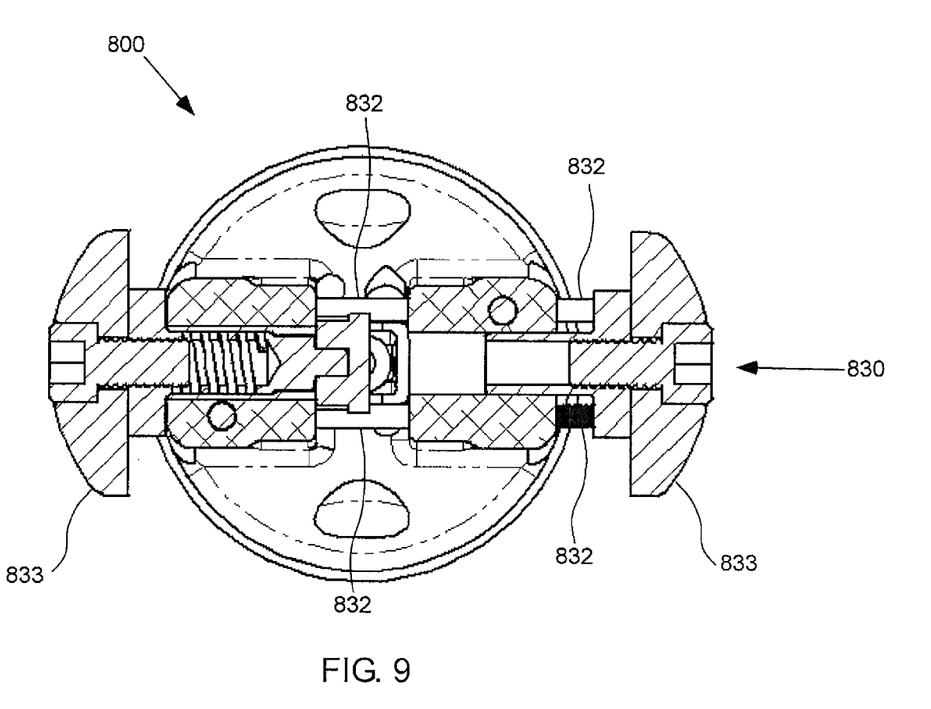
FIG. 9 is a cross sectional view of an embodiment of the invention for a multi-flex wrist.

FIG. 9 illustrates a top view of the multi-flex wrist 800. The lock pins 832 are illustrated in the locked position. Toggling one side of the locking mechanism 830 enables the locking mechanism to be activated or deactivated. In one embodiment, the locking mechanism can be coupled to a first axis to enable the wrist to be locked so that the prosthetic hand is substantially parallel with a user's arm, in a substantially neutral position. This may be beneficial when, for example, using the artificial hand to pick up an object. A second axis can remain unlocked to allow the user to rotate the artificial hand to the right or left. The first axis may also be locked at other predetermined angles to enable a user to perform other tasks. For example, the first axis may be locked such that a prosthetic attachment is locked in one axis at 30 degrees. This can be useful for performing tasks such as driving a vehicle. In another embodiment, both the first and second axes can be placed in a locked position. A user may wish to lock both axes when carrying a heavy load to reduce movement of the load from side to side.

Figure 10:
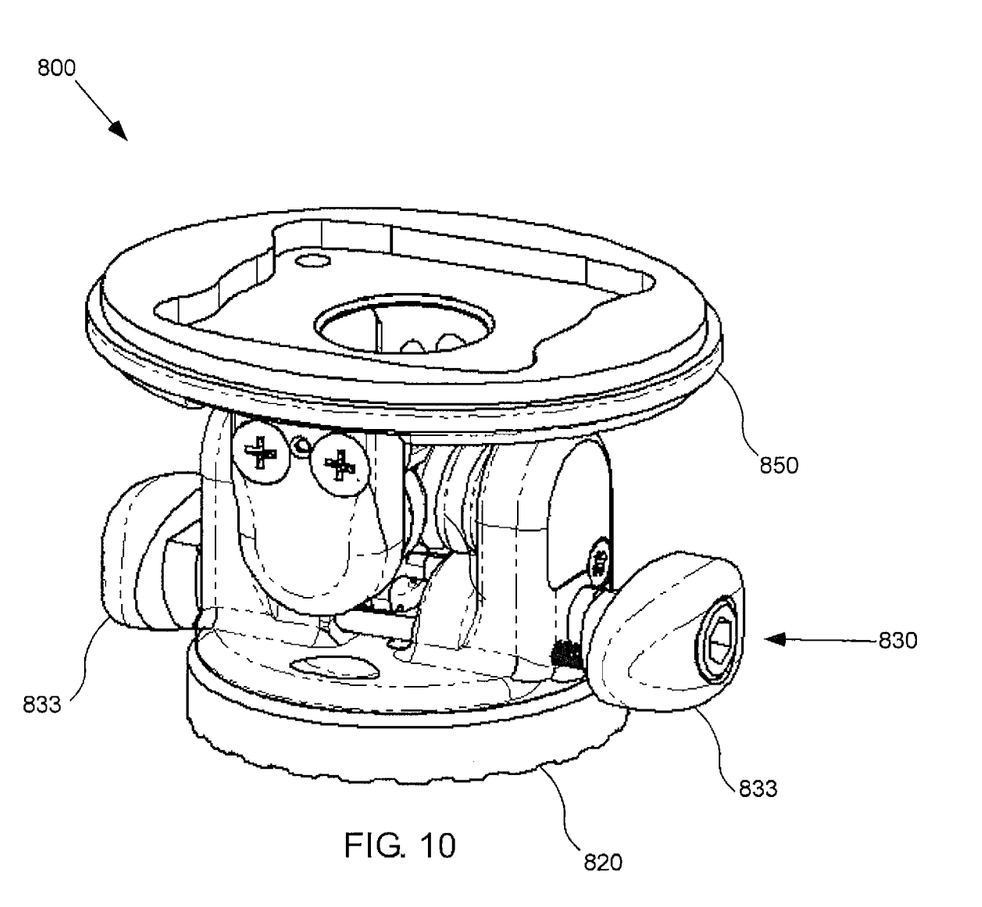
FIG. 10 is a side view of an embodiment of the invention for the a multi-flex wrist.

FIG. 10 illustrates an assembled view of the multi-flex wrist 800. The base 820 is configured for attachment to a prosthetic arm. A device, such as the prosthetic hand 204 shown in FIG. 3, or some other type of attachable device, can be coupled to a quick wrist disconnect plate 850. The cross piece 802, as shown in FIG. 8, can be coupled to the quick wrist disconnect to enable it to rotate in at least two axes. Alternatively, the cross piece can be directly coupled to the prosthetic hand. The locking mechanism 830 can be toggled to enable one or more axes to be temporarily locked at a selected angle.

It is to be understood that the above-referenced arrangements are illustrative of the application for the principles of the present invention. Numerous modifications and alternative arrangements can be devised without departing from the spirit and scope of the present invention while the present invention has been shown in the drawings and described above in connection with the exemplary embodiments(s) of the invention. It will be apparent to those of ordinary skill in the art that numerous modifications can be made without departing from the principles and concepts of the invention as set forth in the claims.

What is claimed is:

1. A multi-axis prosthetic wrist, comprising:
a base plate configured for attachment to a prosthetic arm;
a cross piece coupled to the base plate, the cross piece having a first axis and a second axis;
a prosthetic attachment coupled to the cross piece, wherein the cross piece enables a user to simultaneously flex the prosthetic attachment about the first axis and the second axis;
a first torsional spring coupled to the first axis of the cross piece, wherein the first torsional spring enables the prosthetic attachment to be biased toward a center point; and
a second torsional spring coupled to the second axis of the cross piece; wherein the second torsional spring enables the prosthetic attachment to be biased toward the center point.

2. A multi-axis prosthetic wrist as in claim 1, wherein the cross piece is a universal joint.

3. A multi-axis prosthetic wrist as in claim 1, further comprising a locking mechanism configured to lock one of the first and the second axis to enable the prosthetic attachment to be held at a predetermined angle.

4. A multi-axis prosthetic wrist as in claim 3, wherein the locking mechanism further comprises at least one spring loaded lock pin configured to enable the locking mechanism to be activated or deactivated.

5. A multi-axis prosthetic wrist as in claim 4, wherein the at least one spring loaded lock pin is configured to be inserted into a corresponding locking slot of the cross piece.

6. A multi-axis prosthetic wrist as in claim 3, wherein the locking mechanism is configured to lock the first and second axes.

7. A multi-axis prosthetic wrist as in claim 1, further comprising a plurality of wires used to control the prosthetic attachment, wherein the plurality of wires are routed through an opening in the base plate.

8. A multi-axis prosthetic wrist, comprising:
   a base plate configured for attachment to a prosthetic arm;
   a first axis coupled to the base plate;
   a second axis coupled to the base plate, wherein the second axis is substantially orthogonal to the first axis;
   a prosthetic attachment coupled to the first and second axes, wherein the axes enable a user to simultaneously flex the prosthetic attachment about the first axis and the second axis;
   a first spring coupled to the first axis wherein the first spring enables the prosthetic attachment to be biased toward a center point; and
   a second spring coupled to the second axis wherein the second spring enables the prosthetic attachment to be biased toward the center point.

9. A multi-axis prosthetic wrist as in claim 8, further comprising a locking mechanism configured to lock at least one of the first and the second axis to enable the prosthetic attachment to be held at a predetermined angle.

10. A multi-axis prosthetic wrist as in claim 9, wherein the locking mechanism further comprises at least one spring loaded lock pin configured to enable the locking mechanism to be activated or deactivated.

11. A multi-axis prosthetic wrist as in claim 10, wherein the at least one spring loaded lock pin is configured to be inserted into a corresponding locking slot of the cross piece.

12. A multi-axis prosthetic wrist as in claim 9, wherein the locking mechanism is configured to lock the first and second axes.

13. A multi-axis prosthetic wrist as in claim 8, further comprising a plurality of wires used to control the prosthetic attachment, wherein the plurality of wires are routed through an opening in the base plate.

14. A multi-axis prosthetic wrist as in claim 8, wherein the first spring is a torsional spring.

15. A multi-axis prosthetic wrist as in claim 8, wherein the second spring is a torsional spring.

\* \* \* \* \*